United States Patent
DeGroot et al.

(10) Patent No.: US 6,374,817 B1
(45) Date of Patent: Apr. 23, 2002

(54) APPLICATION OF OP-AMP TO OXYGEN SENSOR CIRCUIT

(75) Inventors: Kenneth P DeGroot, Macomb Township; Claude J. Baxter, Jr., Utica; Bruce H Teague, Grosse Pointe Park, all of MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 0 days.

(21) Appl. No.: 09/547,979

(22) Filed: Apr. 12, 2000

(51) Int. Cl.$^7$ .......................... G01N 27/41; F02D 41/14
(52) U.S. Cl. ...................... 123/672; 123/681; 123/695; 204/406
(58) Field of Search ................... 123/672, 694, 123/695, 693, 703, 704, 699, 698, 696, 688, 681; 204/421, 425, 406

(56) References Cited

U.S. PATENT DOCUMENTS

| | | | |
|---|---|---|---|
| 4,007,589 A | 2/1977 | Neidhard et al. ............. 60/276 |
| 4,088,095 A | 5/1978 | Aono ......................... 123/683 |
| 4,096,839 A | 6/1978 | Niertit ....................... 123/704 |
| 4,140,085 A | 2/1979 | Rabus et al. ................. 123/693 |
| 4,140,086 A | 2/1979 | Schnurie et al. ............. 123/681 |
| 4,163,433 A | 8/1979 | Fujishiro ................... 123/687 |
| 4,167,163 A | 9/1979 | Moder ....................... 123/688 |
| 4,169,439 A | 10/1979 | Tsiang et al. ............... 123/699 |
| 4,197,822 A | 4/1980 | Tsiang ....................... 123/684 |
| 4,208,993 A | 6/1980 | Peter ......................... 123/688 |
| 4,210,106 A | 7/1980 | Wessel et al. ................ 123/696 |
| 4,245,314 A | 1/1981 | Henrich et al. ............. 701/114 |
| 4,263,652 A | 4/1981 | Henrich ....................... 701/115 |
| 4,381,224 A | 4/1983 | Fate et al. ................ 205/784.5 |
| 4,388,903 A | 6/1983 | Yoshida et al. ............. 123/682 |
| 4,440,621 A | 4/1984 | Kitahara et al. ............ 204/406 |
| 4,494,374 A | 1/1985 | Kitahara et al. .............. 60/276 |
| 4,622,126 A | 11/1986 | Shimomura .................. 204/425 |
| 4,705,002 A | * 11/1987 | Ando et al. .................. 123/674 |
| 5,099,818 A | * 3/1992 | Takahashi et al. ........... 123/679 |
| 5,106,481 A | 4/1992 | Rankin et al. ............... 204/426 |
| 5,151,166 A | * 9/1992 | Harral et al. ................ 205/784 |
| 5,263,460 A | 11/1993 | Baxter et al. ............... 123/520 |
| 5,311,853 A | * 5/1994 | Takahashi et al. .......... 123/681 |
| 5,313,121 A | 5/1994 | Cianci et al. ................ 327/103 |
| 5,338,431 A | 8/1994 | Yorita et al. ................ 204/424 |
| 5,461,902 A | 10/1995 | Iwata ........................ 73/23.32 |
| 5,544,640 A | 8/1996 | Thomas et al. ............. 123/689 |
| 5,554,951 A | 9/1996 | Gough ........................ 327/337 |
| 5,596,975 A | 1/1997 | Thomas et al. ............. 123/686 |
| 5,645,745 A | 7/1997 | Hartwick et al. ........... 219/497 |
| 6,021,765 A | 2/2000 | DeGroot et al. ....... 123/568.21 |

* cited by examiner

*Primary Examiner*—John Kwon
*Assistant Examiner*—Hieu T. Vo
(74) *Attorney, Agent, or Firm*—Edwin W. Bacon, Jr.

(57) ABSTRACT

A circuit for improving the resolution of an oxygen sensor in a vehicle exhaust system. The circuit expands a limited output voltage range of an oxygen sensor to full voltage range of an analog-to-digital (A/D) converter, prior to input of the expanded signal into the A/D converter. Utilization of the full range of converter provides improved resolution for analyzing the analog signal.

12 Claims, 3 Drawing Sheets

APPLICATION OF OP-AMP TO OXYGEN SENSOR CIRCUIT

BACKGROUND OF THE INVENTION

1. Field of the Invention

The present invention relates generally to sensor measurements in automobile control systems and, more particularly, to a system for enhancing the precision of an analog sensor reading in an automobile control system.

2. Discussion of Related Art

Current automobile engines are internal combustion engines that use a mixture of fuel and air to generate their driving power. Complete fuel combustion produces only carbon dioxide and water as its products; however, the conditions within an engine do not correspond to the idealized requirements necessary to produce complete combustion. Incomplete combustion produces other products that may include: carbon monoxide, hydrogen gas, hydrocarbons, nitrogen gas, oxygen gas, and various nitrous oxides. Some of these gases are commonly found in the atmosphere and pose few or no health risks. Others can be toxic, creating a desire to reduce such toxic emissions.

The United States and many other countries have strict standards regulating the emissions from automobiles. Catalytic converters transform toxic chemicals into safer compounds. They convert CO, $H_2$, and HC into $CO_2$ and $H_2O$ and also convert nitrous oxides into nitrogen gas and oxygen gas before these gases are emitted from the automobile. Catalytic converters, however, do not completely convert toxic byproducts of incomplete combustion into less harmful substances before emission into the atmosphere. The higher the efficiency of the catalytic converter, the more toxic gases are converted into safer forms before they are emitted into the atmosphere. The efficiency of a catalytic converter relates directly to the composition of its intake gases, and the composition of the intake gases is determined by the combustion conditions, including the air/fuel mixture ratio input to the engine.

The mixture of fuel and air used in the combustion chamber of an engine is regulated through a feedback mechanism. A sensor is placed in the exhaust manifold to measure the oxygen content in the expunged gases. The oxygen content of the combusted mixture varies with respect to where the engine is operating in relation to the stoichiometric point. Typically, the operating point of the engine is called the stoichiometric air/fuel ratio, and this corresponds to the point where the exact quantity of fuel needed for completed combustion is added to the air flow. The stoichiometric point yields the most efficient catalyst operation and produces the least amount of toxic byproducts. The varying operating characteristics of the vehicle change the efficiency of the combustion process and require altering the current fuel flow to maintain engine operating at or near the stoichiometric point. The oxygen sensor output enables optimization of the fuel-air ratio fed into the engine. Optimizing the fuel-air mixture entering the engine changes the combustion conditions and achieves more complete combustion, thereby operating the engine closer to the stoichiometric point.

Oxygen sensors used in most vehicles provide a voltage output that varies in accordance with the amount of oxygen in the combustion product. An analog-to-digital (A/D) converter receives the oxygen sensor output and generates a digital value input to a digital microprocessor. The microprocessor controls the air/fuel ratio and constantly adjusts the mixture entering the combustion chamber in order to maintain the engine operating near the stoichiometric point. Constant adjustment is required because changing engine and environmental conditions alter the efficiency of the combustion process, even for a constant fuel-air mixture ratio. The voltage output of the oxygen sensor varies with the amount of oxygen found in the combustion products.

A typical oxygen sensor functions as a switching device. The switching device outputs less than 0.25 volts when the input air/fuel ratio to the engine is leaner than stoichiometric and outputs greater than 0.75 volts when input air/fuel ratio to the engine is richer than stoichiometric. Due to the physics of the chemical reaction within the oxygen sensor, output voltages are typically limited to less than 1.0 volts.

In the area of ±1 percent of stoichiometric, the output waveform is very steep. In the area outside ±1 percent of stoichiometric, the output waveform is nearly flat. Within the area of ±1 percent of stoichiometric, minor changes in the oxygen content found in combustion products result in significant changes in the output voltage of the oxygen sensor. Conversely, outside of ±1 percent of stoichiometric, even significant changes in the oxygen content in the combustion products result in predictably small changes in the output voltages of the oxygen sensor. The steep characteristic of the oxygen sensor in the stoichiometric region makes measuring the prevailing operating point difficult.

As discussed above, most controllers utilize a A/D converter to covert the analog output voltage of the oxygen sensor into a digital value for use by an electronic engine controller. A typical A/D converter converts a voltage range that varies between 0 and 5 volts into an 8-bit digital value for use by the engine controller. An 8-bit digit value can vary between 0 and 255, yielding 256 gradations or counts. The 256 counts in the typical A/D converter translate into approximately 0.0196 volts per count. Because the normal output of the oxygen sensor varies between a voltage range of 0 to 1 volts, only counts 0 to 51 of the 256 possible counts are utilized to determine the value of the analog signal received from the oxygen sensor. Thus, only approximately 20 percent of the total range of the A/D converter is utilized. This limited resolution reduces the level of oxygen sensor output detail input to the engine control system. This reduced resolution is particularly important in the critical zone around stoichiometric where minor variations in the oxygen content of the combusted products result in large variations in the voltage output by the oxygen sensor.

Thus, there is a need to improve the resolution of the oxygen sensor signal applied to the A/D converter in the engine control system.

SUMMARY OF THE INVENTION

A control system for regulating the fuel and air mixture used in an engine. The control system includes an engine producing drive power through combustion of fuel and air. An analog sensor connected to the engine monitors a concentration of gases produced through the combustion of fuel and air in the engine. The analog sensor generates an analog signal that varies in accordance with the concentration. The output signal is within a first predetermined voltage range. An amplifier receives the analog signal and amplifies the analog voltage to generate an amplified signal. The amplified signal is within a second predetermined voltage range, wherein the second voltage range is greater than the first voltage range. An analog-to-digital (A/D) converter receives the analog signal and generates a digital signal that varies in accordance with the amplified signal. The A/D converter converts input voltages varying within the second voltage range. A microprocessor receives the digital signal from the A/D converter and produces a mixture signal that varies in accordance with a desired fuel and air mixture, wherein the desired mixture varies in accordance with the analog signal.

These and other advantages and features of the present invention will become readily apparent from the following detailed description, claims and drawings.

DETAILED DESCRIPTION OF THE PREFERRED EMBODIMENTS

The following discussion of the preferred embodiments directed to the precision enhancement of reading an analog sensor in an automobile control system is merely exemplary in nature and is in no way intended to limit the invention or its applications or uses.

Figure 1:
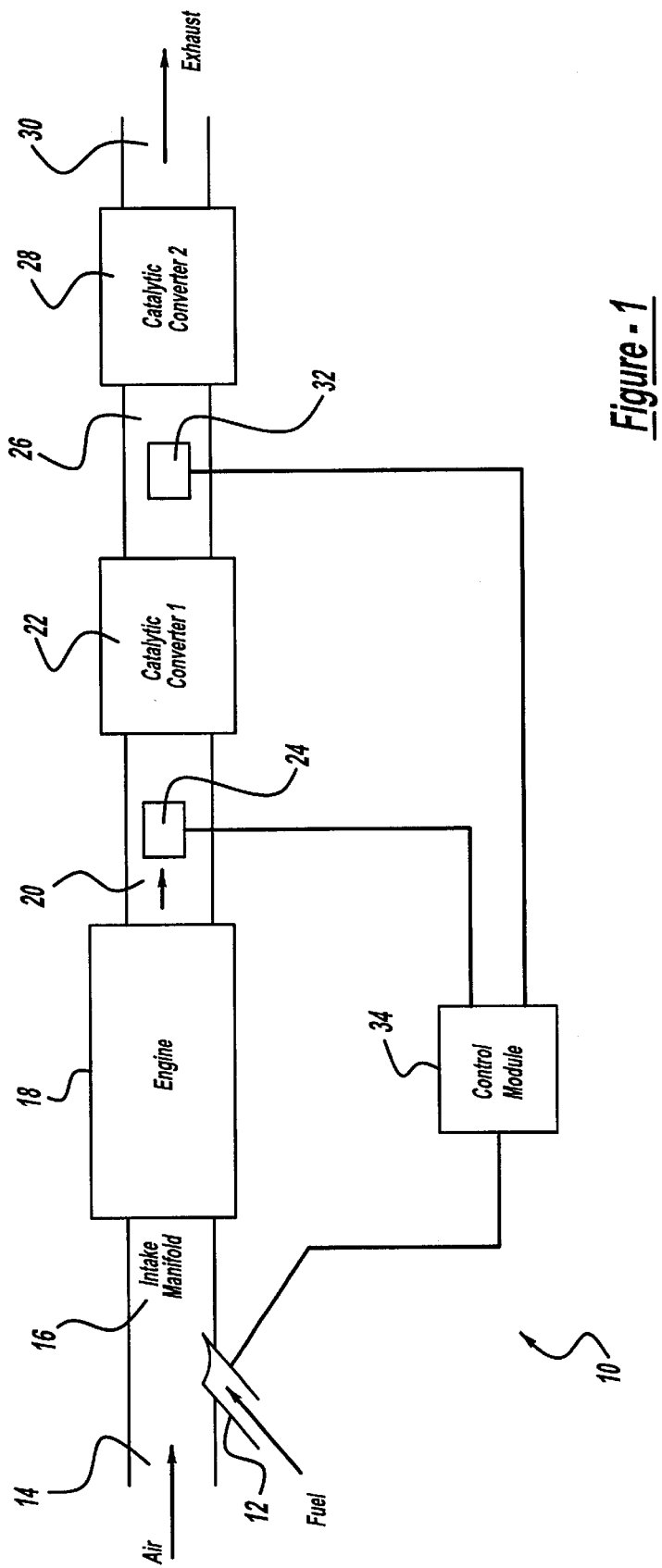
FIG. 1 is a block diagram of the exhaust and air/fuel control system of an automobile.

FIG. 1 is a flow diagram of the exhaust and fuel control system 10 of a vehicle. Fuel 12 and air 14 are fed separately into the intake manifold 16 where they are mixed together. The air/fuel mixture is fed into engine 18 where it is combusted to produce drive power for the vehicle. The combustion of fuel 12 and air 14 produces various byproducts that are expelled from the engine 18 after combustion. The combustion byproducts are generically termed the combustion exhaust 20, 26. The combustion exhaust 20 is fed into a catalytic converter 22. Catalytic converter 22 reacts the various toxic byproducts from the exhaust gases into safer compounds before emission as exhaust 26. Optionally, a second catalytic converter 28 performs a similar function as first catalytic converter 22 to further remove toxic byproducts from exhaust 26 before emission as exhaust 30. The efficiency of catalytic converters 22, 28 varies with the composition of the combustion exhaust 20, 26. The composition of the respective combustion exhaust 20, 26 varies with the fuel-air mixture and the engine's operating conditions.

A first sensor 24 monitors combustion exhaust 20 emitted from the engine 18. A second sensor 32 monitors exhaust 26 output by first catalytic converter 22. Sensors 24, 32 examine the byproducts produced by the combustion process and feed this information back to the air/fuel mixture control module 34. The air/fuel mixture control module 34 adjusts the ratio of the fuel 12 and air 14 in the mixture sent to the engine 18 and thereby alters the composition of the combustion exhaust 20, 26. The adjustment of the air/fuel mixture allows the engine 18 to operate closer to the stoichiometric point. At this point, catalytic converters 22, 28 operate at or near peak efficiency so that the vehicle emits the least amount of toxic byproducts.

Sensors 24, 32 are embodied as oxygen sensors. Sensors 24, 32 measure the amount of oxygen present in the exhaust gas emitted from engine 18 after combustion. Sensors 24, 32 operate as a voltage source and produce an output between approximately 0 and 1 volts based on the amount of oxygen present in the respective combustion exhaust 20, 26. The less the amount of oxygen present (lower air/fuel ratio) in the combustion exhaust 20, 26, the greater the voltage outputted by respective sensors 24, 32. The amount of oxygen present in the combustion exhaust 20, 26 enables determination where in relation to the stoichiometric point the engine 18 is operating and how the air/fuel mixture should be adjusted to move engine 18 closer to the stoichiometric operating point.

Figure 2:
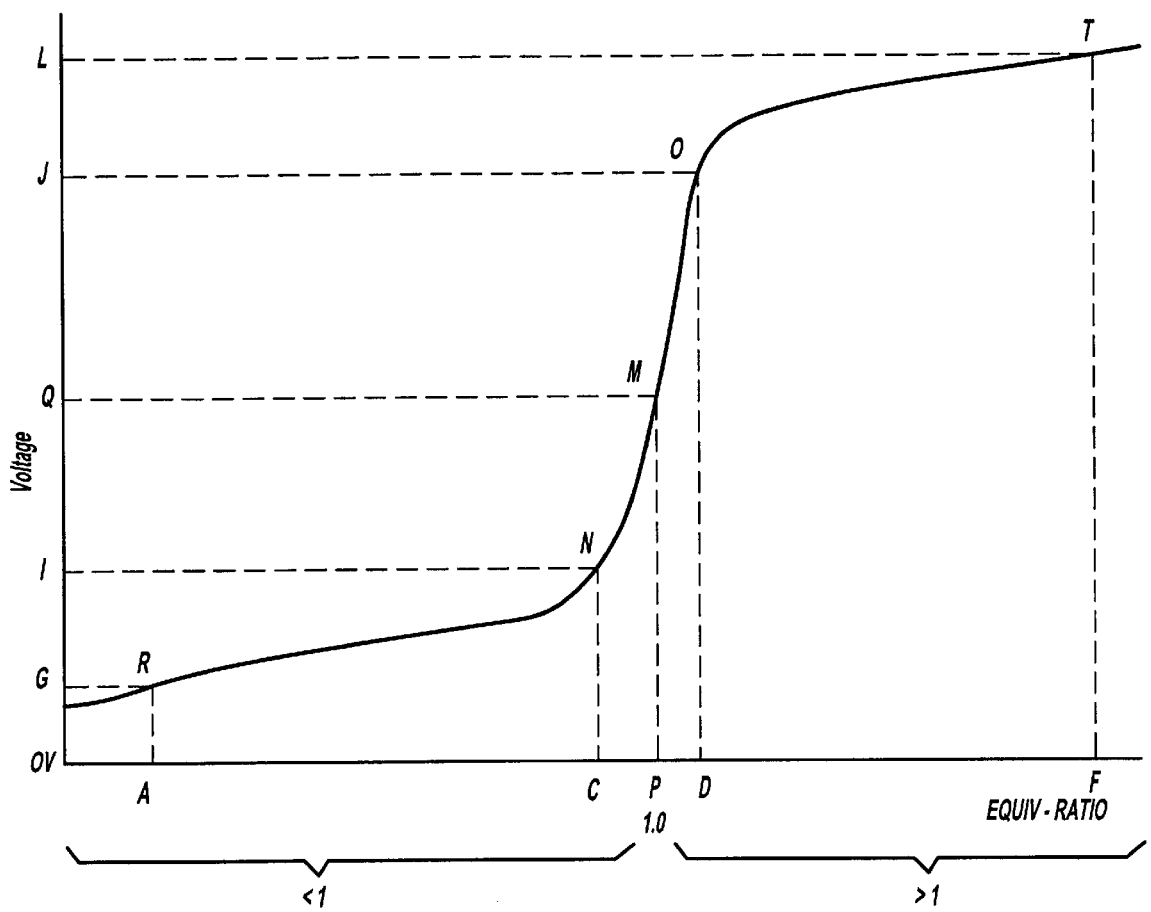
FIG. 2 is a graph of the relative equivalence ratio in the combustion exhaust versus voltage output by the oxygen sensor.

FIG. 2 shows a typical operating curve of an exemplary oxygen sensor, such as oxygen sensors 24, 32. Operation will be described with respect to oxygen sensor 24, but is equally applicable to oxygen sensor 32. The x-axis represents the equivalence ratio of combustion exhaust, and the y-axis represents and the output voltage of oxygen sensor 24. The stoichiometric operating point M represents the point at which the combustion in the engine 18 is closest to complete. At this point the catalytic converters 22, 28 operate most efficiently. The equivalence ratio range P to F represents a rich mixture of fuel to oxygen. In this range, relatively little oxygen is present after the combustion process. The equivalence ratio range P to A represents a lean mixture of fuel to oxygen. In this range, the amount of oxygen emitted after the combustion process is relatively great. In both of these ranges the combustion of the engine 18 is not fully complete, and while this does not greatly affect the performance of the engine 18, the efficiency of the catalytic converters 22, 28 drops and fewer compounds are removed from the exhaust gas.

The stoichiometric operating point M corresponds to a set voltage output Q from the oxygen sensor. It should be noted that this point does not necessarily correspond to exactly half the value of the maximum output of the oxygen sensor and this point may vary along the curve, between N and O, during normal vehicle operation.

The range of the curve from N to O around the stoichiometric point M is very steep. Moving from point N to O on the curve represents a small change in the equivalence ratio of the combustion exhaust. The steep portion of the curve spans an equivalence ratio of C to D. This small air/fuel ratio change represents a significant voltage change from points I to J on the y-axis. Because a small equivalence ratio change corresponds to a significant oxygen sensor output voltage change, utilizing only a small range of an A/D converter to cover the entire output voltage range of the oxygen sensor reduces the precision in determining at which point along the air/fuel curve the engine 18 is operating. This is particularly relevant when attempting to take measurements along the steep portion of the curve.

Figure 3:
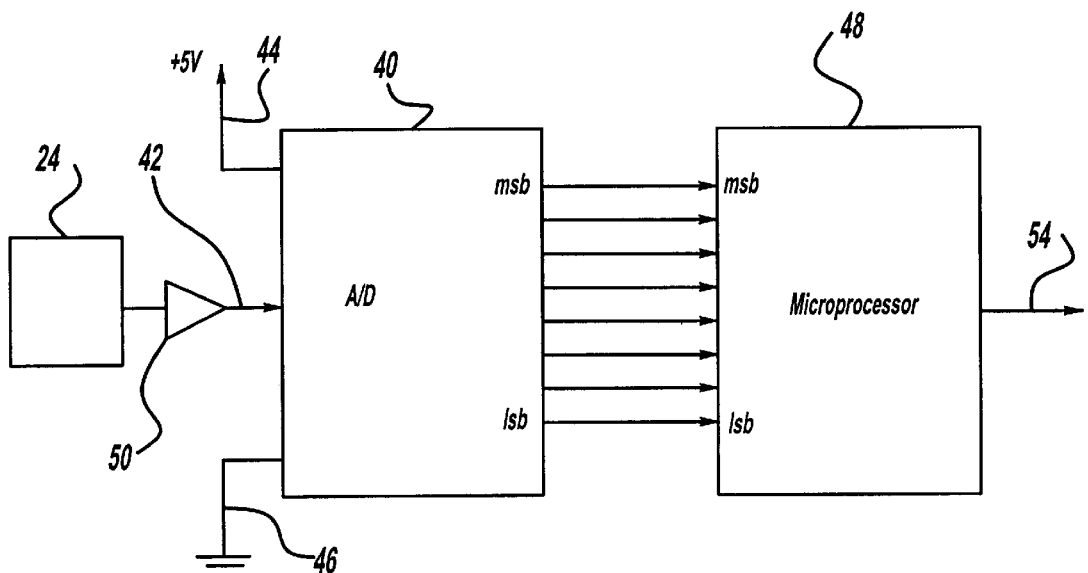
FIG. 3 is a block diagram of the analog-to-digital converter and microprocessor of the controller of FIG. 1.

FIG. 3 depicts a block diagram for converting the analog signal output by the oxygen sensor to a digital signal to enable adjustment of the air/fuel mixture input to engine 18. The block diagram of FIG. 3 will be described with respect to oxygen sensor 24, but is equally applicable to oxygen sensor 32. The analog output of the sensor 24 is input to amplifier circuit 50. The output of amplifier circuit 50 is input to analog-to-digital (A/D) converter 40. A/D converter 40 converts the analog signal output by amplifier circuit 50 into a digitally encoded n-bit word. As described herein A/D converter 40 is an 8-bit A/D converter.

A/D converter 40 operates using a supply voltage 44 and a ground reference 46. The 8-bit word defines $2^8=256$ counts, where a zero count corresponds to zero volts and a 256 count corresponds to 5 volts. Preferably, the signal output by amplifier circuit 50 ranges from ground reference 46 to the supply voltage 44 to yield maximum resolution.

As discussed above, oxygen sensors 24, 32 generally output a voltage within the range of 0 to 1 volts. As also discussed above, this implies that the full range of A/D converter 40 spans 0 to 51 counts, or approximately twenty percent of the overall possible resolution. Accordingly, amplifier circuit 50 receives the signal output by oxygen sensor 24 and scales the signal output by oxygen sensor 24 to a full input range for A/D converter 40. In this particular example, the full range of A/D converter 40 is 0 to 5 volts. Because the full range of the signal output by oxygen sensor 24 is 0 to 1 volts, a scale factor or gain of 5 is applied to the signal in order to expand the signal to the full 0 to 5 volts range of A/D converter 40. The signal output by oxygen sensor 24 is thus scaled to the full input range of A/D converter 40 so that the full 256 available counts can be used to determine the oxygen content of the exhaust gas. The 8-bit word is then input to microprocessor 48 which determines an air/fuel error mixture signal which is output by control module 34 of FIG. 1.

Figure 4:
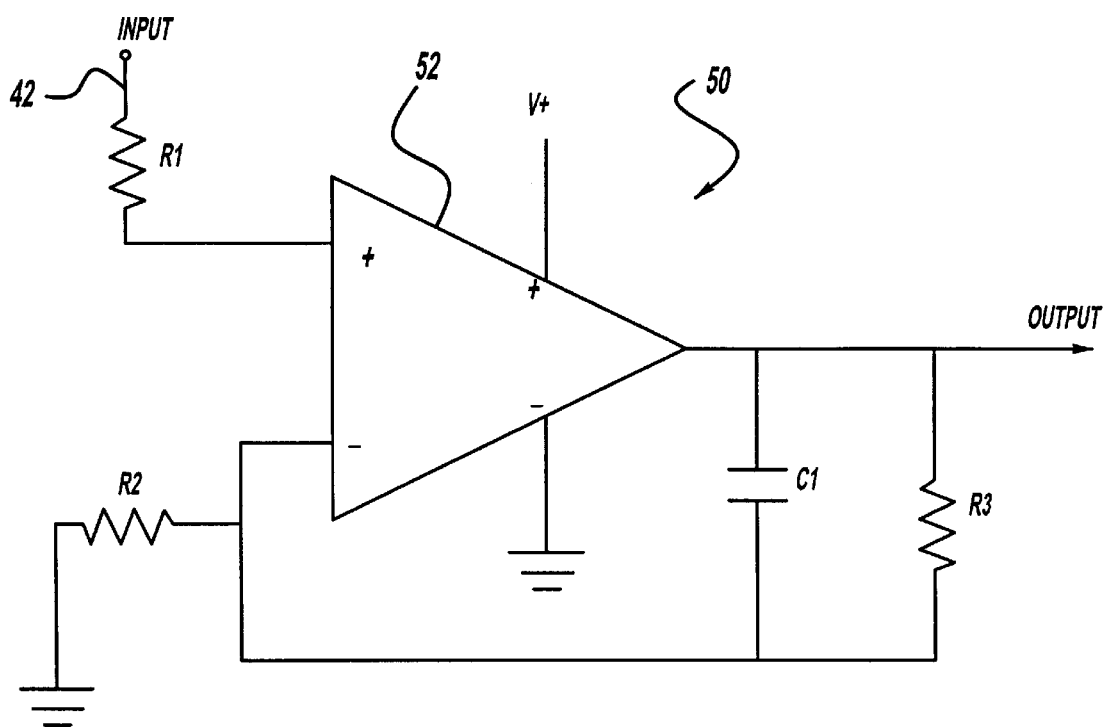
FIG. 4 is a circuit diagram of the amplifier of FIG. 3.

FIG. 4 depicts a circuit diagram for amplifier circuit 50 of FIG. 3. The signal output by oxygen sensor 24 is applied to the non-inverting terminal of an operational amplifier 52 through a resistor R1. The inverting terminal of operational amplifier 52 is connected to ground through a resistor R2. Operational amplifier 52 is powered by a voltage signal V+ and also includes a reference voltage connected to ground. The output of operational amplifier 52 defines an amplified signal which is then input to A/D converter 40. The output from operational amplifier 52 is fed back to the inverting terminal through a feedback resistor R3. A capacitor C1 is inserted in the feedback loop in order to minimize noise. Through proper selection of resistors R3 and R2, the gain of amplifier circuit 50 can be varied in accordance with the function (1+R3/R2). In the present embodiment, the components of amplifier circuit 50 have the following values:

| Component | Value |
|---|---|
| R1 | 1 kΩ |
| R2 | 15 kΩ |
| R3 | 60 kΩ |
| C1 | 0.0015 μf |

The exemplary values discussed in the above table define an amplifier circuit 50 having a gain of 5. Accordingly, the signal output by oxygen sensor 24 having a voltage range of 0 to 1 volt has been expanded by amplifier circuit 50 to the full range of A/D converter, 0 to 5 volts.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A control system for regulating the fuel and air mixture used in an engine, the system comprising:
   an engine producing drive power through combustion of fuel and air;
   an analog sensor operably connected to the engine, the analog sensor monitoring a concentration of gases produced through the combustion of fuel and air in the engine, the analog sensor generating an analog signal that varies in accordance with the concentration, the analog signal being within a first predetermined voltage range;
   an amplifier, the amplifier receiving the analog signal and amplifying the analog signal to generate an amplified signal, the amplified signal being within a second predetermined voltage range, wherein the second voltage range is greater than the-first voltage range; and
   a mixture control module including an analog-to-digital (AID) converter and a microprocessor, the A/D converter receiving the amplified signal and generating a digital signal that varies in accordance with the amplified signal, the A/D converter being adapted to convert input voltages varying within the second voltage range, the microprocessor receiving the digital signal from the A/D converter and producing a mixture signal that varies in accordance with a desired fuel and air mixture, wherein the output of the microprocessor alters the fuel and air mixture provided by the mixture control module to the engine.

2. The system of claim 1 where the analog sensor is an oxygen sensor, the oxygen sensor measuring the oxygen content in the combustion exhaust and generating the analog signal in accordance with the content of oxygen in the combustion exhaust.

3. The system of claim 2 wherein the first voltage range is 0 volts to 1.0 volts.

4. The system of claim 3 wherein the second voltage range is 0 volts to 5 volts.

5. The system of claim 4 wherein the first voltage range is 0 volts to 1.0 volts.

6. The system of claim 5 wherein the second voltage range is 0 volts to 5 volts.

7. A control system for regulating the fuel and air mixture used in an engine, comprising:
   an engine producing drive power through combustion of fuel and air;
   an analog sensor operably connected to the engine, the analog sensor monitoring a concentration of gases produced through the combustion of fuel and air in the engine, the analog sensor generating an analog signal that varies in accordance with the concentration, the analog signal being within a first predetermined voltage range;
   an amplifier, the amplifier receiving the analog signal and amplifying the analog signal to generate an amplified signal, the amplified signal being within a second predetermined voltage range, wherein the second voltage range is greater than the first voltage range;
   an analog-to-digital (A/D) converter, the A/D converter receiving the amplified signal and generating a digital signal that varies in accordance with the amplified signal, the A/D converter being adapted to convert input voltages varying within the second voltage range; and
   a microprocessor, the microprocessor receiving the digital signal from the A/D converter and producing a signal that varies in accordance with a desired fuel and air mixture, wherein the desired mixture varies in accordance with the analog signal.

8. The system of claim 7 where the analog sensor is an oxygen sensor, the oxygen sensor measuring the oxygen content in the combustion exhaust and generating the analog signal in accordance with the content of oxygen in the combustion exhaust.

9. The system of claim 8 wherein the first voltage range is 0 volts to 1.0 volts.

10. The system of claim 9 wherein the second voltage range is 0 volts to 5 volts.

11. The system of claim 7 wherein the first voltage range is 0 volts to 1.0 volts.

12. The system of claim 11 wherein the second voltage range is 0 volts to 5 volts.

* * * * *